(12) United States Patent
Root et al.

(10) Patent No.: US 10,768,407 B2
(45) Date of Patent: Sep. 8, 2020

(54) EMBEDDABLE MODULE FOR HIGH OUTPUT LED

(71) Applicant: Acera, LLC, Beverly, MA (US)

(72) Inventors: Thomas V. Root, Beverly, MA (US); Thomas Davis, Hollis, NH (US); Michael Cook, Salem, MA (US); Carlton Jones, Boxford, MA (US); David Leo, Winchester, MA (US); Michael S. Epstein, Saint Michaels, MD (US)

(73) Assignee: Acera, LLC, Beverly, MA (US)

( * ) Notice: Subject to any disclaimer, the term of this patent is extended or adjusted under 35 U.S.C. 154(b) by 0 days.

(21) Appl. No.: 16/686,863

(22) Filed: Nov. 18, 2019

(65) Prior Publication Data

US 2020/0081241 A1    Mar. 12, 2020

Related U.S. Application Data

(63) Continuation of application No. 15/338,027, filed on Oct. 28, 2016.
(Continued)

(51) Int. Cl.
*G02B 23/24* (2006.01)
*G02B 6/42* (2006.01)
(Continued)

(52) U.S. Cl.
CPC ........ *G02B 23/2453* (2013.01); *A61B 1/0011* (2013.01); *A61B 1/00126* (2013.01);
(Continued)

(58) Field of Classification Search
CPC . A61B 1/0011; A61B 1/00126; F21V 29/773; F21V 29/89; G02B 23/2453
See application file for complete search history.

(56) References Cited

U.S. PATENT DOCUMENTS

| 2,908,197 A | 10/1959 | Wells et al. |
| 3,285,242 A | 11/1966 | Wallace |

(Continued)

FOREIGN PATENT DOCUMENTS

| CN | 205079073 U | 3/2016 |
| EP | 2846179 A2 | 3/2015 |

(Continued)

OTHER PUBLICATIONS

International Preliminary Report on Patentability for corresponding PCT Application No. PCT/US2016/059361, dated May 11, 2018, 10 pages.

(Continued)

*Primary Examiner* — Leah Simone Macchiarolo
(74) *Attorney, Agent, or Firm* — Nelson Mullins Riley & Scarborough LLP; Thomas J. Engellenner; Reza Mollaaghababa

(57) ABSTRACT

In one aspect, a light module is disclosed, which includes a housing providing a hollow chamber extending from a proximal end to a distal end, and a lens positioned in the hollow chamber, where the lens has a lens body comprising an input surface for receiving light from a light source and an output surface through which light exits the lens body, said lens further comprising a collar at least partially encircling said lens body. The light module further includes at least one shoulder on which the lens collar can be seated for positioning the lens within the housing. A light source, e.g., an LED, is coupled to the hollow chamber, e.g., at its proximal end, for providing light to the lens.

8 Claims, 30 Drawing Sheets

Related U.S. Application Data

(60) Provisional application No. 62/247,456, filed on Oct. 28, 2015, provisional application No. 62/247,454, filed on Oct. 28, 2015, provisional application No. 62/247,451, filed on Oct. 28, 2015.

(51) Int. Cl.

| | | |
|---|---|---|
| *A61B 1/00* | (2006.01) | |
| *A61B 1/06* | (2006.01) | |
| *F21V 5/04* | (2006.01) | |
| *A61B 1/07* | (2006.01) | |
| *G02B 19/00* | (2006.01) | |
| *H05B 45/10* | (2020.01) | |
| *G02B 1/04* | (2006.01) | |
| *F21V 8/00* | (2006.01) | |
| *F21V 29/77* | (2015.01) | |
| *F21V 29/89* | (2015.01) | |
| *F21L 4/00* | (2006.01) | |
| *F21V 15/01* | (2006.01) | |
| *F21V 23/04* | (2006.01) | |
| *F21V 23/06* | (2006.01) | |
| *F21V 3/00* | (2015.01) | |
| *F21V 17/12* | (2006.01) | |
| *G02B 6/38* | (2006.01) | |
| *F21Y 115/10* | (2016.01) | |
| *F21L 14/02* | (2006.01) | |
| *F21W 131/20* | (2006.01) | |
| *F21W 131/40* | (2006.01) | |

(52) U.S. Cl.
CPC ............ *A61B 1/0669* (2013.01); *F21L 4/005* (2013.01); *F21V 3/00* (2013.01); *F21V 5/04* (2013.01); *F21V 5/048* (2013.01); *F21V 15/01* (2013.01); *F21V 17/12* (2013.01); *F21V 23/0414* (2013.01); *F21V 23/06* (2013.01); *F21V 29/773* (2015.01); *F21V 29/89* (2015.01); *G02B 1/041* (2013.01); *G02B 6/0006* (2013.01); *G02B 6/0008* (2013.01); *G02B 6/4206* (2013.01); *G02B 6/428* (2013.01); *G02B 6/4231* (2013.01); *G02B 6/4269* (2013.01); *G02B 19/0066* (2013.01); *G02B 23/2469* (2013.01); *H05B 45/10* (2020.01); *A61B 1/00105* (2013.01); *A61B 1/07* (2013.01); *F21L 4/00* (2013.01); *F21L 14/02* (2013.01); *F21W 2131/20* (2013.01); *F21W 2131/40* (2013.01); *F21Y 2115/10* (2016.08); *G02B 6/3807* (2013.01)

(56) References Cited

U.S. PATENT DOCUMENTS

| | | | |
|---|---|---|---|
| 3,592,199 A | 7/1971 | Ostensen | |
| 4,414,608 A * | 11/1983 | Furihata | A61B 1/00117 352/198 |
| D331,634 S | 12/1992 | Browne | |
| 5,353,208 A | 10/1994 | Moore | |
| 5,682,199 A * | 10/1997 | Lankford | A61B 1/00105 348/65 |
| 5,702,349 A * | 12/1997 | Morizumi | A61B 1/00188 600/131 |
| 5,743,848 A | 4/1998 | Koeda et al. | |
| 6,007,485 A * | 12/1999 | Koeda | A61B 1/00126 600/178 |
| 6,099,147 A | 8/2000 | Ziegenfuss | |
| 6,135,947 A | 10/2000 | Watanabe et al. | |
| 6,257,741 B1 | 7/2001 | Williams et al. | |
| 6,540,389 B1 * | 4/2003 | Novak | G02B 6/0008 362/551 |
| 6,819,505 B1 | 11/2004 | Cassarly et al. | |
| 6,937,791 B2 | 8/2005 | Guy | |
| 6,991,603 B2 | 1/2006 | Krupa et al. | |
| 7,115,091 B2 | 10/2006 | Root et al. | |
| D533,939 S | 12/2006 | Root et al. | |
| 7,193,519 B2 | 3/2007 | Root et al. | |
| 7,198,397 B2 | 4/2007 | Bennett et al. | |
| 7,229,201 B2 | 6/2007 | Krupa et al. | |
| D551,762 S | 9/2007 | Root et al. | |
| D561,336 S | 2/2008 | Laflash et al. | |
| D581,052 S | 11/2008 | Root et al. | |
| D623,786 S | 9/2010 | Wessel | |
| 7,798,692 B2 | 9/2010 | Krupa et al. | |
| D629,537 S | 12/2010 | Hsu et al. | |
| D631,567 S | 1/2011 | Lodhie | |
| 8,033,704 B2 | 10/2011 | Krupa et al. | |
| 8,152,715 B2 | 4/2012 | Root et al. | |
| D662,231 S | 6/2012 | Sakamoto et al. | |
| D663,445 S | 7/2012 | Sakamoto et al. | |
| D663,464 S | 7/2012 | Lee | |
| D666,340 S | 8/2012 | Sakamoto et al. | |
| D669,200 S | 10/2012 | Chen et al. | |
| D671,241 S | 11/2012 | Sakamoto et al. | |
| D671,242 S | 11/2012 | Sakamoto et al. | |
| D671,243 S | 11/2012 | Sakamoto et al. | |
| D675,349 S | 1/2013 | Parker et al. | |
| D685,506 S | 7/2013 | Pickard et al. | |
| D690,383 S | 9/2013 | Sheikh et al. | |
| 8,801,253 B2 | 8/2014 | Krupa et al. | |
| D715,463 S | 10/2014 | Jun | |
| 9,022,628 B2 | 5/2015 | Krupa et al. | |
| 9,055,863 B2 | 6/2015 | Krupa et al. | |
| D739,586 S | 9/2015 | Hong | |
| D744,674 S | 12/2015 | Wu et al. | |
| D753,322 S | 4/2016 | Taylor | |
| D760,928 S | 7/2016 | Bao | |
| D768,321 S | 10/2016 | Inskeep | |
| D775,752 S | 1/2017 | Nook et al. | |
| D778,473 S | 2/2017 | Cooper | |
| D793,595 S | 8/2017 | Lesperance et al. | |
| D804,064 S | 11/2017 | Taylor et al. | |
| D810,325 S | 2/2018 | Guo | |
| D813,424 S | 3/2018 | Shum et al. | |
| D836,227 S | 12/2018 | Root | |
| 2003/0009084 A1 * | 1/2003 | May | A61B 1/00188 600/112 |
| 2004/0213001 A1 | 10/2004 | Sayers et al. | |
| 2004/0218858 A1 | 11/2004 | Guy | |
| 2004/0246744 A1 | 12/2004 | Krupa et al. | |
| 2005/0162848 A1 | 7/2005 | Dalton et al. | |
| 2005/0201100 A1 | 9/2005 | Cassarly et al. | |
| 2006/0183977 A1 * | 8/2006 | Ishigami | A61B 1/00177 600/179 |
| 2007/0173695 A1 * | 7/2007 | Hirata | A61B 1/053 600/152 |
| 2007/0253188 A1 | 11/2007 | Klipstein et al. | |
| 2008/0027408 A1 | 1/2008 | Wilson et al. | |
| 2008/0039715 A1 | 2/2008 | Wilson et al. | |
| 2008/0174996 A1 | 7/2008 | Lu et al. | |
| 2008/0194973 A1 | 8/2008 | Imam | |
| 2009/0040783 A1 | 2/2009 | Krupa et al. | |
| 2009/0185392 A1 | 7/2009 | Krupa | |
| 2010/0226127 A1 | 9/2010 | Bigliatti et al. | |
| 2010/0277894 A1 | 11/2010 | Kim | |
| 2011/0194295 A1 | 8/2011 | Householder et al. | |
| 2013/0046172 A1 | 2/2013 | Waitzman et al. | |
| 2015/0219313 A1 | 8/2015 | Marcaly | |
| 2017/0122525 A1 | 5/2017 | Root et al. | |
| 2017/0123131 A1 | 5/2017 | Root et al. | |
| 2017/0123199 A1 * | 5/2017 | Jones | F21V 17/12 |
| 2019/0361217 A1 | 11/2019 | Root et al. | |

FOREIGN PATENT DOCUMENTS

| | | |
|---|---|---|
| JP | 2015077336 A | 4/2015 |
| WO | 2008016895 A2 | 2/2008 |

(56) References Cited

FOREIGN PATENT DOCUMENTS

| | | |
|---|---|---|
| WO | 2008017718 A1 | 2/2008 |
| WO | 2015038971 A1 | 3/2015 |

OTHER PUBLICATIONS

International Search Report/Written Opinion for corresponding PCT Application No. PCT/US2016/059361, dated Apr. 4, 2017, 16 pages.
International Search Report/Written Opinion for corresponding PCT Application No. PCT/US2016/059406, dated Apr. 7, 2017, 9 pages.
International Search Report/Written Opinion for corresponding PCT/US2016/059451, dated Jun. 19, 2017; 15 pages.
Invitation to Pay Additional Fees and, Where Applicable, Protest Fee, for PCT/US2016/059451, dated Mar. 16, 2017; 6 pages.
Invitation to Pay Additional Fees for corresponding PCT Application No. PCT/US2016/059361, dated Feb. 3, 2017, 6 pages.
European Search Report, 16794163.2, dated Jan. 7, 2020, 7 pages.
International Search Report and Written Opinion, PCT/US2019/069111, dated Mar. 25, 2020, 24 pages.

\* cited by examiner

EMBEDDABLE MODULE FOR HIGH OUTPUT LED

RELATED APPLICATIONS

The present application is a continuation application of a patent application entitled "Embeddable Module For High Output LED" having an application Ser. No. 15/338,027 filed on Oct. 28, 2016, which claims priority to a provisional patent application entitled "Embeddable module for light output LED" having an application No. 62/247,454 filed on Oct. 28, 2015, and a provisional patent application entitled "Elliptical optical lens for high output LED" having an application No. 62/247,451 filed on Oct. 28, 2015, and a provisional patent application entitled "Handheld mobile light source" having an application No. 62/247,456 filed on Oct. 28, 2015, each of which is herein incorporated by reference in its entirety.

The present application is also related to utility patent applications entitled "Elliptical optical lens for high output LED" and "Handheld mobile light source" that are being filed concurrently herewith and are hereby incorporated by reference in their entirety.

BACKGROUND

The present invention relates generally to a light module that can be embedded in a variety of devices, such as endoscopes, to provide light for illuminating a field of view. In many embodiments, the light module can provide high intensity, low heat light.

SUMMARY

In one aspect, a light module is disclosed, which includes a housing (e.g., a handheld housing) providing a hollow chamber extending from a proximal end to a distal end, and a lens positioned in the hollow chamber, where the lens has a lens body comprising an input surface for receiving light from a light source and an output surface through which light exits the lens. The lens further includes a collar that at least partially encircles the lens body. The light module further includes at least one shoulder disposed in the hollow chamber and in contact with the lens collar for providing mechanical support to the lens. By of way of example, the shoulder can be provided by at least one sleeve placed in contact with the lens collar to provide mechanical support to the lens. A light source is coupled to the hollow chamber at the proximal end thereof (e.g., positioned within the hollow chamber) for providing light to the input surface of the lens. In some embodiments, the light module can include an optical window disposed in the hollow chamber and optically coupled to the output surface of the lens such that the light exiting the lens passes through the optical window before exiting the light module. In many embodiments, the lens can be removably and replaceably positioned in the hollow chamber.

A variety of light sources can be employed. In some embodiments, the light source can include one or more light emitting diodes (LEDs). A variety of LEDs emitting radiation at different wavelengths, such as wavelengths in the ultraviolet, infrared, far-infrared, and visible portions of the electromagnetic spectrum can be employed.

The optical window can be formed of a variety of different materials. Some examples of suitable materials include, without limitation, sapphire, quartz, and glass. In some embodiments, the window can also function as a filter for blocking certain wavelengths of light while allowing other wavelengths to pass therethrough. For example, the optical window can function as a high pass, a low pass or a bandpass filter. By way of example, the optical window can block ultraviolet and infrared wavelengths while allowing visible wavelengths to pass therethrough.

In some embodiments, the light module further includes a retaining window that is removably and replaceably coupled to the light module's housing, e.g., at its distal end. By way of example, in some such embodiments, the retaining window can include a plurality of threads that can removably and replaceably engage with a plurality of threads (e.g., internal threads) provided at the distal end of the light module's housing.

In some embodiments, the retaining window can include an internal channel extending from a proximal opening to a distal opening for coupling via the distal opening to a light guide, e.g., via an adapter to which the light guide is connected.

In some embodiments, a gasket can be disposed between the retaining window and the optical window to provide a seal therebetween. In some such embodiments, the retaining window presses against the gasket to provide the seal and further provide mechanical support to the optical window.

The light source (e.g., an LED) can be mounted on a printed circuit (PC) board disposed within the module's housing, e.g., at its proximal end. The board can include a plurality of electrical leads for coupling the light module to a source of power for supplying power to the light source. Further, a plate can be connected to the proximal end of the module's housing to facilitate securely holding the above components within the housing and in some cases to facilitate sealing the interior of the housing from the external environment. The plate can include a plurality of openings through which the electrical leads can protrude for connecting to a source of power.

In some embodiments, the lens includes a lens body extending from a proximal section having said input surface to a distal section having said output surface. The proximal section further comprises a substantially elliptical peripheral surface receiving at least a portion of the light entering the lens body via said input surface and directing at least some of the received light via total internal reflection to the distal section such that at least a portion of the light directed to the distal section exits the lens body through said output surface. The peripheral elliptical surface can be characterized by a proximal focal point and a distal focal point. In some embodiments, the distal focal point is positioned external to the lens, e.g., a distance above the output surface of the lens. For example, the distal focal point may be positioned outside the lens body at a distance above the lens's output surface so as to be within a proximal portion of the light guide upon coupling of the light guide to the light module. In other embodiments, the distal focal point may be positioned in the distal section of the lens body. In some embodiments, the distal focal point may be positioned at the output surface of the lens. Further, in some embodiments, the proximal focal point of the elliptical surface can be positioned, e.g., at the light source or in close proximity thereto.

In some embodiments, the lens collar is disposed at the boundary between the proximal and distal sections of the lens body.

In some embodiments, the lens can have an input surface having a central convex portion and a peripheral portion surrounding the central convex portion. In some embodiments, the peripheral portion of the input surface is shaped such that at least a portion of the light entering the lens body via the peripheral portion propagates to the peripheral elliptical surface to be reflected thereby. In some embodiments, the peripheral portion of the input surface is shaped such that at least about 80%, or at least about 90%, or at least about 95% (and preferably 100%) of the light entering the lens body via that portion propagates to the peripheral surface of the lens body to be reflected thereby. In some embodiments, the peripheral portion of the input surface includes a proximal concave segment and a distal convex segment.

In some embodiments, the convex portion of the input surface and/or the elliptical peripheral surface can exhibit a positive optical power in a range of about 50 to about 300 D. In some embodiments, the convex portion of the input surface is configured such that the light entering the lens body via that portion propagates to the lens' output surface without striking the elliptical peripheral surface.

In some embodiments, the input surface forms a cavity configured to receive at least partially the light source. In some embodiments, the proximal focal point of the elliptical peripheral surface is positioned in the cavity.

In some embodiments, the input surface of the lens is configured to capture at least about 80%, or at least about 90%, or at least about 95% (and preferably 100%) of the light emitted by the light source.

In some embodiments, the lens body is rotationally symmetric about an optical axis and its output surface is substantially flat and orthogonal to that axis.

Various components of the light module can be formed of a variety of different materials. For example, the lens can be formed of any suitable polymeric material, such as polycarbonate, polymethylmethacrylate (PMMA). In some cases in which the LED emits radiation in the infrared region of the electromagnetic spectrum, the lens may be formed of high density polyethylene (HDPE). In some embodiments, the module's housing and/or the sleeves can be formed of a metal or a plastic.

In a related aspect, a light module is disclosed, which includes a housing providing a hollow chamber extending from a proximal end to a distal end, and a lens positioned in the hollow chamber, where the lens has a lens body comprising an input surface for receiving light from a light source, an output surface through which light exits the lens body and a peripheral elliptical surface that directs light incident thereon via total internal reflection to the output surface, said lens further comprising a collar at least partially encircling the lens body. The light module further includes at least one shoulder on which the lens collar can be seated for positioning the lens within the housing. A light source, e.g., an LED, is coupled to the hollow chamber, e.g., at its proximal end, for providing light to the lens. In some embodiments, an optical window is disposed in the hollow chamber and is optically coupled to the output surface of the lens such that the light exiting the lens passes through the optical window before exiting the light module. In some embodiments, the shoulder can be formed as part of the housing. In other embodiments, the shoulder can be provided by a sleeve disposed in the module's housing.

In a related aspect, a device for providing illumination to a field of view is disclosed, which includes a housing, a removable and replaceable light module coupled to the housing, and one or more light guide(s) mechanically coupled to the housing and optically coupled to the light module to receive light therefrom. In some embodiments, the housing includes an enclosure for receiving the light module. In some such embodiments, the light guide(s) are disposed within the housing and in optical coupling with the light module to receive light therefrom. The light guide(s) can extend to an opening within the housing through which the light exiting the light guide(s) can exit the device to illuminate a field of view. By way of example, the device can be an endoscope, a surgical headlight, a video camera, a retractor, a speculum, and other devices requiring high intensity, high quality light.

By way of example, such a device can be an endoscope. In some such embodiments, the endoscope can be a single-use endoscope.

In a related aspect, a light module is disclosed, which includes a housing providing a hollow chamber extending from a proximal end to a distal end, a lens positioned in said hollow chamber, said lens having a lens body comprising an input surface for receiving light from a light source and an output surface through which light exits the lens body, said lens further comprising a collar at least partially encircling said lens body. The light module further includes at least one shoulder on which said collar is seated. A light source is coupled to the hollow chamber at the distal end for providing light to the input surface of the lens.

In some embodiments, an optical window (formed, e.g., of sapphire or quartz) is disposed in the hollow chamber and is optically coupled to the output surface of the lens such that the light exiting the lens passes through the window before exiting the light module.

In some embodiments, the light module includes at least one sleeve disposed in the hollow chamber, which provides the shoulder for holding the lens. In some embodiments, the shoulder is formed as protrusion extending into the housing from the inner wall of the housing.

In some embodiments, the lens includes a peripheral surface for receiving at least a portion of the light entering the lens body via said input surface and for directing said received light via total internal reflection to the output surface. In some embodiments, the peripheral surface has a truncated elliptical shape characterized by an input focus and an output focus. In some such embodiments, the input focus is positioned on or in proximity of the light source and the output focus is positioned external to said lens at a distance above said output surface of the lens. In other embodiments, the output focus is positioned inside the lens, e.g., below the output surface or at the output surface of the lens.

In some embodiments, the light module can include a retaining window removably and replaceably coupled to the distal end of the housing. The retaining window can be configured for coupling to an adapter housing one or more light guides for optically coupling said light guides to the light module.

Further understanding of various aspects of the invention can be obtained by reference to the following detailed description in conjunction with the associated drawings, which are described briefly below.

DETAILED DESCRIPTION

Figure 1:
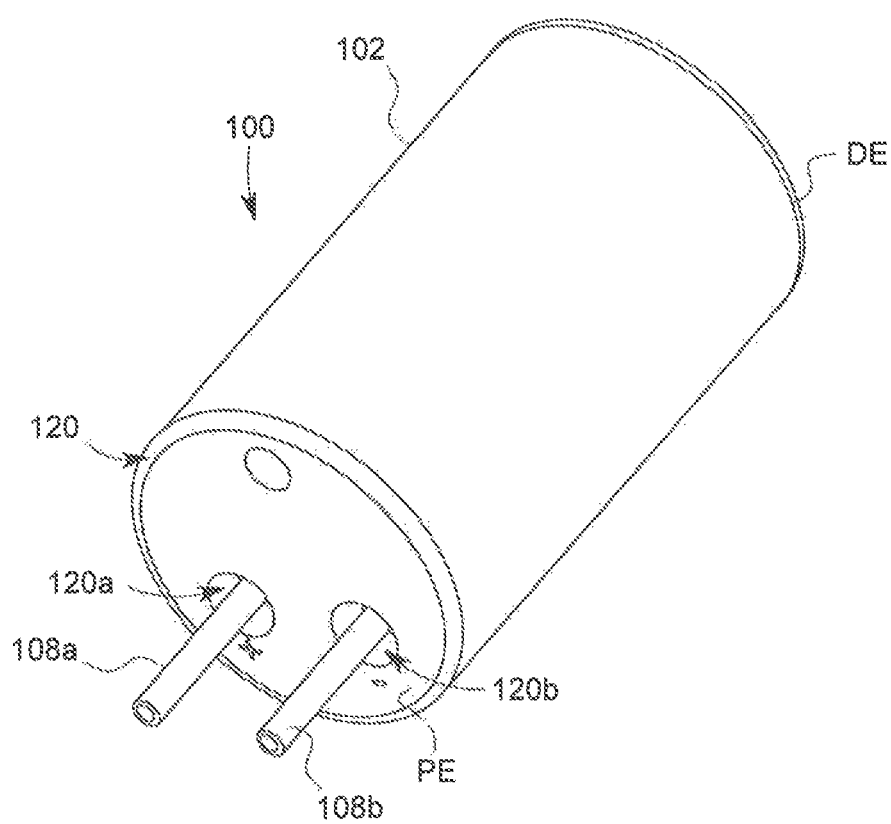
FIG. 1 is a schematic view of a light module according to an embodiment of the present teachings.

The present invention generally relates to a light module that can be incorporated in a variety of devices, such as medical and industrial endoscopes, to provide light for illuminating a field of view when the devices are employed for their intended purpose. As discussed in more detail below, in many embodiments, the light module can be removably and replaceably embedded in a device, such as an endoscope, to efficiently transfer light emitted by a light emitting diode (LED) to a light guide (e.g., an optical fiber or a bundle of optical fibers) of the device. In particular, in many embodiments, the light module employs a lens for collecting light emitted by an LED over a large angular extent and to converge that light for efficient coupling into a light guide.

Various terms are used herein consistent with their common meanings in the art. By way of further explanation, a number of terms are defined below:

The term "optical power" is used herein consistent with its common meaning in the art to refer to the degree to which an optical component or surface converges or diverges incident light and is equal to the reciprocal of the focal length of the component of the surface.

The term "numerical aperture" is used herein consistent with its common meaning in the art to refer to a dimensionless number that characterizes the range of angles over which an optical component or system can emit or accept light.

The term "elliptical surface" or similar terms as used herein refer to a surface that is shaped as a section of an ellipse. In other words, an elliptical surface is in the form of a truncated ellipse.

The term "about" as used herein is intended to indicate a variation of at most 10% around a numerical value.

The term "substantially" as used herein is intended to indicate a deviation of less than 5% relative to a complete state or condition.

With reference to FIGS. 1, 2A, 2B, and 3, a light module 100 according to an embodiment of the present teachings includes a substantially cylindrical housing 102 that provides a hollow chamber 104 extending from a proximal end (PE) to a distal end (DE). As discussed in more detail below, the hollow chamber 104 can accommodate a plurality of components of the light module.

More specifically, the light module 100 includes a printed circuit board 106 on which a light emitting diode (LED) 108 is mounted. The circuit board 106 includes a pair of electrical leads 108a/108b for coupling the circuit board to a source of electrical power for supplying electrical power to the LED 108 and in some cases controlling the intensity of the light emitted by the LED 108. In some embodiments, the LED 108 can have an emitting surface of approximately 1 mm×1 mm, and can be coated with a wavelength conversion material (such as phosphorus) to emit a broadband continuum of visible light, e.g., at wavelengths between about 470 and 700 nm. In some embodiments, the light emitted by the LED 108 has a divergence angle (i.e., the angle within which about 90% of the light is emitted) of about 160 degrees. In some embodiments, the LED 108 is a high-power LED (such as Luxeon III Model LXHL-LW3C), which can be operated at a typical forward voltage of 3.7 V and a typical operating current of 700 mA. In general, a variety of the LEDs can be employed, including, LEDs providing radiation at a variety of different wavelengths, such as 430 nm, 470 nm, near infrared, infrared, or visible. In some embodiments, multiple LEDs can be employed.

The light module 100 further includes a lens 112 having a lens body 112a providing an input surface 114 forming a cavity for at least partially receiving the LED 108. At least a portion of the light emitted by LED enters the lens body via the input surface 114. In some embodiments, the input surface 114 receives at least about 80%, or at least about 90%, or at least about 95% (and preferably 100%) of the light emitted by the LED 108. The lens 112 further includes an output surface 116 through which light can exit the lens body. As discussed further below, the lens 112 further includes a collar 118 that partially encircles the lens body. The collar 118 includes a lower surface 118a and an upper surface 118b.

In some embodiments, the light exits the lens with a numerical aperture in a range of about 0.5 to about 0.9, e.g., 0.66 or 0.88. In some embodiments, the lens is configured such that the numerical aperture associated with the light exiting the lens allows efficient coupling of the light into a light guide that is optically coupled to the output surface of the lens to receive light therefrom. For example, in some embodiments, the numerical aperture associated with the light exiting the lens can be substantially equal to an input numerical aperture of an optical fiber (or a bundle of optical fibers) receiving light from the lens. A plurality of different types of light guides can be employed. For example, the light guide can be a single optical fiber, a bundle of optical fibers (e.g., a plurality of square or round-shaped optical fibers), a liquid light guide, a plurality of tapers made from glass or plastic to form a light guide, etc.

A bottom plate 120 is coupled to the proximal end of the hollow shell 104, which provides a seat for the circuit board 106. The bottom plate 120 includes a pair of openings 120a and 120b through which the electrical leads 108a/108b can protrude for coupling to a source of electrical power.

In this embodiment, the light module also includes a pair of sleeves 122/124 disposed on opposite sides of the lens collar. In this embodiment, each of the sleeves 122/124 is in the form of a cylindrical shell. More specifically, the sleeve 122 includes an annular shell 122a extending between a bottom annular surface 122b and a top annular surface 122c. When assembled within the hollow chamber 104, the bottom annular surface 122b of the sleeve 122 is seated on an outer portion of the circuit board and the top annular surface 122c is in contact with the lower annular surface of the lens collar 118 to provide a seat for the lens.

The sleeve 124 similarly includes an annular shell 124a extending between a bottom annular surface 124b to a top annular surface 124c. When assembled within the hollow chamber 104, the bottom annular surface 124b is in contact with the upper annular surface 118b of the lens collar. In this manner, the two sleeves 122 and 124 facilitate positioning the lens within the hollow chamber 104 and provide mechanical support for the lens.

In this embodiment, the light module includes an optical window 126 that is optically coupled to the output surface 116 of the lens 112 such that the light exiting the lens (or at least a portion of that light) passes through the optical window 126 before exiting the light module. More specifically, when assembled within the hollow chamber 104, the optical window 126 is seated on the top annular surface 124c of the sleeve 12. In this embodiment, the optical window is in the form of a disk having lower and upper flat faces 126a and 126b. In some embodiments, the optical window can have a thickness in a range of about 0.5 mm to about 2 mm, though other thicknesses can also be employed.

The optical window 126 can protect the output surface of the lens. In addition, in some embodiments, the optical window 126 can adjust one or more characteristics of the light exiting the lens. By way of example, the optical window 126 can be selected to function as a filter, e.g., a bandpass filter, to allow passage of certain wavelengths of the light exiting the lens while blocking other wavelengths. For example, such filtering of the light exiting the lens can be used to adjust the color temperature of the light. The optical window 126 can be formed of a variety of different materials, such as sapphire, quartz, glass, etc. In some embodiments, the material from which the optical window 126 is formed is substantially transparent to visible radiation. In other embodiments, the optical window 126 may be substantially transparent to radiation in another region of the electromagnetic spectrum. By way of example, in some embodiments in which the light module emits radiation in the infrared region of the electromagnetic spectrum, the optical window 126 can be formed of high density polyethylene.

The light module 100 further includes a retaining window 128 (herein also referred to as a ring window) that can be removably and replaceably coupled to the distal end of the housing 102. More specifically, with reference to FIGS. 2A and 2B, in this embodiment, the retaining window 128 includes a plurality of external threads 128a that can engage with a plurality of internal threads 102a provided at the distal end of the housing 102a. The retaining window 128 has an annular shape providing an internal channel 129 extending from a lower opening 129a to an upper opening 129b for accommodating a light guide adapter, as discussed in more detail below. The retaining window 128 includes a plurality of internal threads 128b for engaging the retaining window with the light guide adapter.

A gasket 127 is positioned between the retaining window 128 and the optical window 126 such that when the components are assembled within the hollow chamber 104 the retaining window presses against the gasket to facilitate holding the optical window in place and providing a seal.

Figure 3:
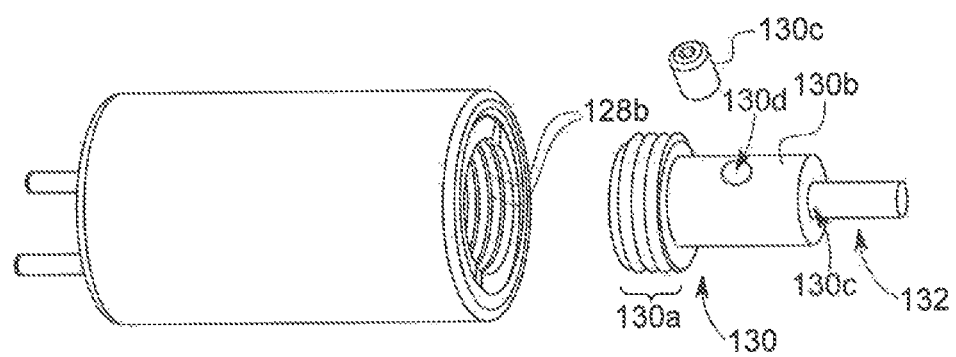

With reference to FIG. 3, the retaining window 128 can be removably and replaceably coupled to an adapter 130, where the adapter can be in turn coupled to a light guide (e.g., an bundle of optical fibers) 132. In this embodiment, the adaptor 130 includes a plurality of external threads 130a that can engage with the internal threads 128b of the retaining window to removably and replaceably couple the adapter to the retaining window.

In this embodiment, the 130 adapter includes a substantially cylindrical housing 130b having an central hollow channel 130c for receiving the light guide 132. The housing includes an opening 130d for receiving a retaining pin 130e, which secures the light guide 132 within the adapter 130.

In some embodiments, an input surface(s) of the light guide 130 can be in contact with the upper surface 126a of the optical window 126. In other embodiments, the input surface(s) of the optical fiber can be positioned at a small distance from the upper surface 126a of the optical window 126. In some embodiments, the input surface(s) of the light guide is substantially flat and has an area substantially equal to an illuminated area of the upper surface of the optical window so as to allow efficient coupling of the light into the light guide. In some embodiments, a refractive index-matching material, such as a gel or an adhesive cement, can be applied to the upper surface 126a of the optical window 126 to facilitate efficient coupling of the light into the light guide.

As noted above, a plurality of different types of light guides can be employed. For example, the light guide 132 can be a single optical fiber, a bundle of optical fibers (e.g., a plurality of square or round-shaped optical fibers), a liquid light guide, a plurality of tapers made from glass or plastic to form a light guide, etc.

In some embodiments, the light module transmits light emitted by the LED 108 to a light guide coupled to the light module via the retaining window with an efficiency of at least about 30%, or at least about 40%, or at least about 50%, or at least about 60%, or at least about 70%, or at least about 80%, or at least about 90%, or at least about 95%. In other words, the light module transfer at least about 30%, or at least about 40%, or at least about 50%, or at least about 60%, or at least about 70%, or at least about 80%, or at least about 90%, or at least about 95% of the light emitted by the LED to the light guide. In some embodiments, the numerical aperture associated with the light exiting the light module to be coupled to a light guide is selected so as to optimize efficient coupling of the light into the light guide. For example, the optical module can be configured for efficient coupling of light into an optical fiber having an input numerical aperture of about 0.5, 0.66, or 0.88. Further, optical fibers having a plurality of sizes can be employed to receive light from the light module. For example, fibers having a diameter of about 2.1 mm, about 3 mm, about 3.4 mm, about 4 mm, about 5 mm, or about 6 mm can be employed. For each fiber size, the lens can be configured, e.g., by adjusting the curvature of its peripheral surface, the size of its output surface, to provide efficient coupling of the light emitted by the LED 108 into the optical fiber, or a bundle of optical fibers.

Table 1 below presents theoretically simulated efficiency of various implementations of the light module 100 for coupling light into fibers of different sizes, where the lens size refers to the diameter of the output surface of the lens. The data presented in Table 1 shows that even for a fiber size as small as 2.1 mm, the light module can couple light emitted by an LED efficiently into the fiber. Further, the data shows that a lens size of 4 mm, efficient optical coupling of the light into different fiber sizes can be achieved.

TABLE 1

|  |  | Fiber size (mm) | | | | | | |
|---|---|---|---|---|---|---|---|---|
|  |  | 2.1 | 3.0 | 3.4 | 4.0 | 4.5 | 5.0 | 6.0 |
| Lens | 3.0 | 38.9 | 64.2 | 64.3 | 64.4 | 64.5 | 64.5 | 64.7 |
| size | 3.4 | 36.2 | 61.0 | 70.1 | 70.9 | 70.2 | 70.3 | 70.4 |
| (mm) | 4.0 | 31.6 | 55.6 | 65.5 | 76.1 | 76.2 | 76.2 | 76.3 |
|  | 5.0 | 21.2 | 42.3 | 52.8 | 67.6 | 76.8 | 82.5 | 82.6 |
|  | 6.0 | 15.7 | 33.1 | 42.5 | 57.3 | 68.6 | 77.1 | 85.6 |

The light modules according to the present teachings provide a number of advantages. For example, such light modules can be embedded and easily adapted for use with multiple types of different types of illumination devices. By way of example, the light modules according to the present teachings may be embedded within medical or industrial endoscopes, video cameras, retractors, speculums, surgical headlights and other devices requiring high intensity, high quality light.

Figure 4:
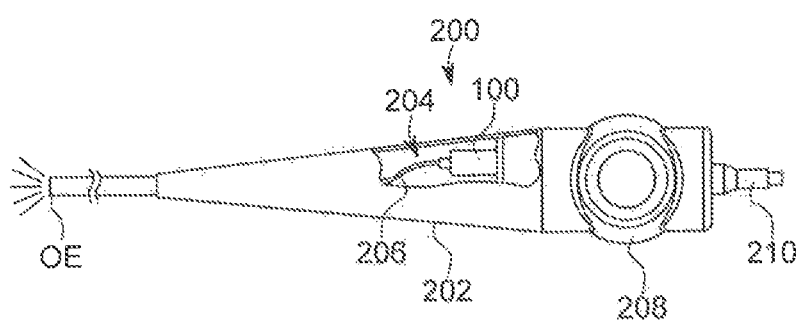

By way of example, FIG. 4 schematically depicts an endoscope 200 according to an embodiment of the present teachings in which the light module 100 is incorporated. More specifically, the endoscope 200 includes a body 202 providing an enclosure 204 for removably and replaceably receiving the light module 100. The endoscope 200 further includes one or optical fibers 210 that are optically coupled to the light module to receive light therefrom. The optical fibers extend to a distal end (DE) of the endoscope through which the light exits the endoscope to illuminate a field of view. The endoscope 200 can further include a light detector (not shown) and one or more optical components (not shown), such as lenses, mirrors, for directing light emanating from a field of view to the detector to form an image of the field of view, in a manner known in the art. Further, the exemplary endoscope 200 can include processing circuitry for forming the image and transmitting the image via a proximal connector 210 to a monitor (not shown) for viewing, e.g., by a medical professional. The exemplary endoscope 200 can also include a user interface element 208 that allows a user to manipulate the endoscope.

Figure 5:
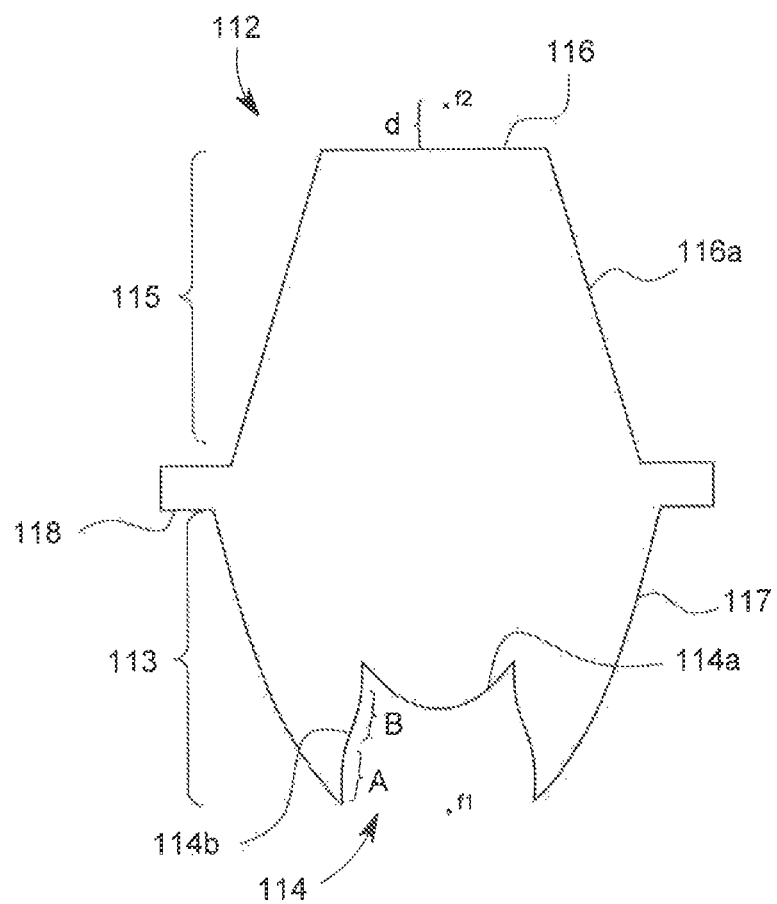
FIG. 5 is a schematic cross-sectional view of lens suitable for use in a light module according to the present teachings.

As noted above, in this embodiment, the lens 112 includes an input surface 114, and output surface 116 and an elliptical peripheral surface 115 that is configured to reflect light incident thereon via total internal reflection. By way of further illustration, FIG. 5 schematically depicts that the lens 112 includes a proximal section 113 having the input surface 114 for receiving light from the LED 108 and a distal section 115 having the output surface 116 through which the light exits the lens and a peripheral surface 116a. In this embodiment, the peripheral surface 116a of the distal section 115 of the lens is in the form of a truncated cone, though in other embodiments it can have a different shape. The collar 118 is positioned at the border between the proximal section and the distal section. In this embodiment, the input surface 114 of the lens 112 forms a cavity and includes a central convex portion 114a surrounded by a peripheral portion 114b. In this embodiment, the peripheral portion 114b of the input surface includes a proximal concave segment (A) and a distal convex segment (B). The proximal section 113 includes an elliptical peripheral surface 117 that is in the form of a truncated ellipse having two foci f1 (herein referred to as the input focus) and f2 (herein referred to as the output focus). The focus f1 is positioned in the input cavity on or in proximity of the LED and the other focus f2 is positioned external to the lens at a distance (d), e.g., in a range of about 4 mm to about 6 mm, above the output surface 116. In many embodiments, the output focus f2 is positioned so as to be within a proximal section of a light guide optically coupled to the lens to ensure efficient coupling of the light exiting the lens into the light guide.

In other embodiments, the output focus f2 can be within the lens body, e.g., below the lens' output surface or at the output surface. In some embodiments, the position of the distal focal point 1240 is selected such that the light rays diverging from the distal focal point exhibit an angular spread across the input face of a light guide coupled to the lens that maximizes the coupling of the light into the light guide. For example, the diverging beam can have an angular spread commensurate with an input numerical aperture of the light guide.

In some embodiments, any of the convex portion 114a and the elliptical peripheral surface 117 exhibits a positive optical power in a range of about 50 Diopters to about 300 Diopters, though other optical powers can also be employed. In some other embodiments, the convex portion is configured such that its focal point (i.e., the point at which the light rays refracted by that portion converge) is external to the lens. By way of example, the focal point of the convex portion may be within the proximal end of a light guide coupled to the lens, or external to both the lens and the light pipe such that the light rays diverging form the focal point to illuminate the input face of the light pipe would exhibit a maximum angular spread corresponding to that of a solid angle subtended by the input face of the light guide. By way of example, in some such embodiments, the focal point of the convex portion can be substantially coincident with the distal focal point of the elliptical peripheral surface.

The lens 112 can be formed of any suitable material, such as a variety of different polymeric materials. Some examples of such materials include, without limitation, polymethylmethacrylate (PMMA), and polycarbonate. In some embodiments in which the LED 106 emits radiation in the infrared region of the electromagnetic spectrum, the lens may be formed of high density polyethylene to be substantially transparent to that radiation wavelength. In some embodiments, the proximal and distal sections of the lens as well as the lens' collar are formed as a single integral unit, e.g., using molding or other manufacturing techniques known in the art.

Figure 2A:
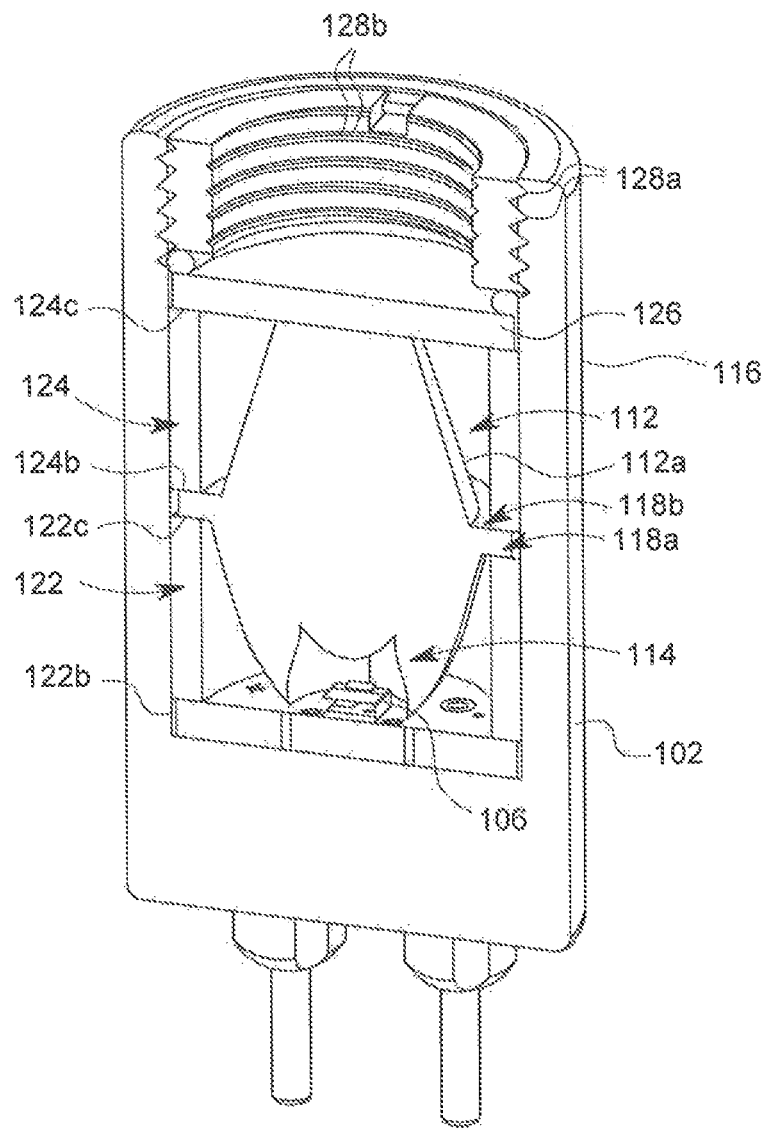
FIG. 2A is a cross-sectional view of the light module depicted in FIG. 1 illustrating various components thereof.
Figure 2B:
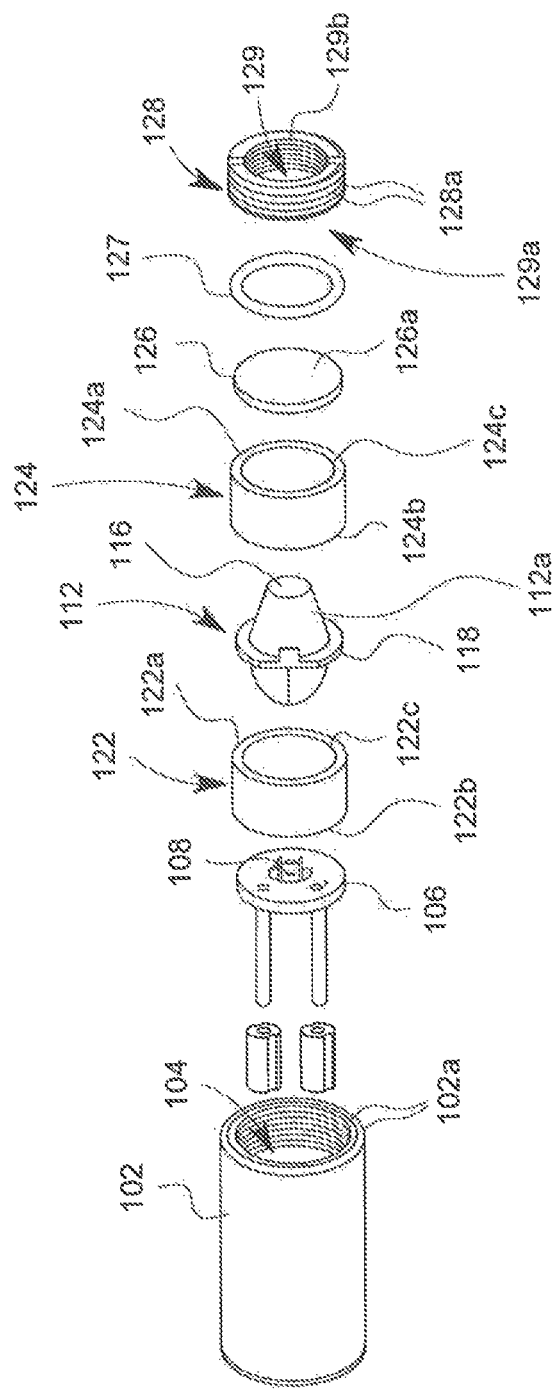
FIG. 2B is a schematic exploded view of the light module depicted in FIG. 1, FIG. 3 schematically shows the light module of FIG. 1 and a light guide adapter that can be coupled to the light module, FIG. 4 schematically depict an exemplary endoscope in which a light module according to the present teachings in embedded.

With reference to FIG. 2A as well as FIG. 5, in some embodiments, the lens 112 is coupled to the LED 106 such that the distance between the LED and the convex portion 114a of the input surface is less than about 0.3 mm, or less than about 0.2 mm. In some cases, the distance between the LED 106 and the convex portion 114a of the input surface is about 0.24 mm.

Figure 6:
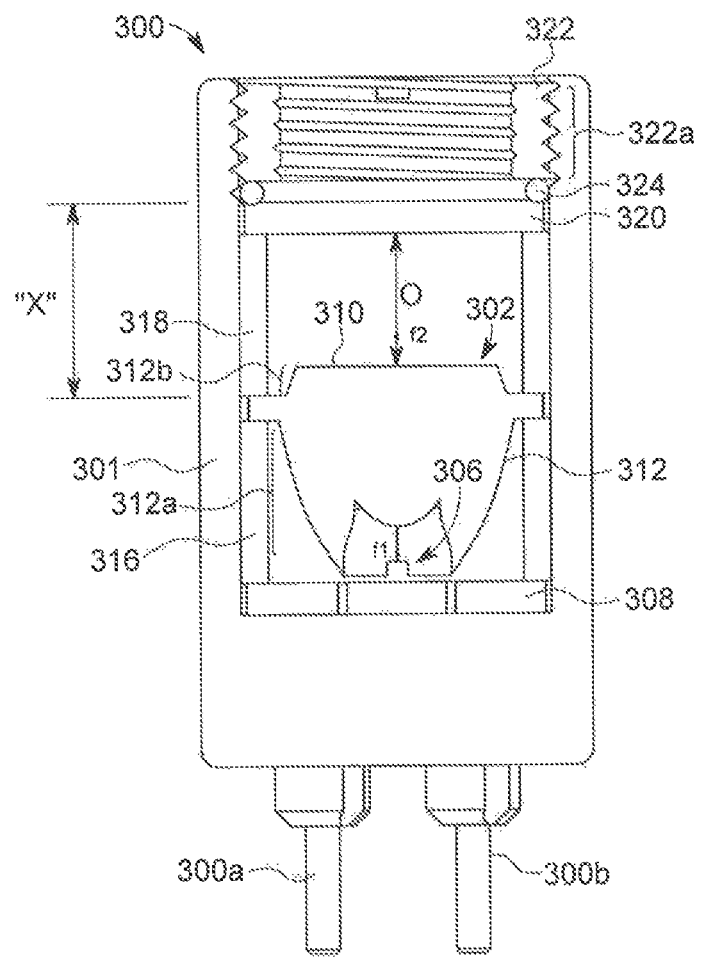
FIG. 6 is a schematic cross-sectional view of a light module according to another embodiment.
Figure 7:
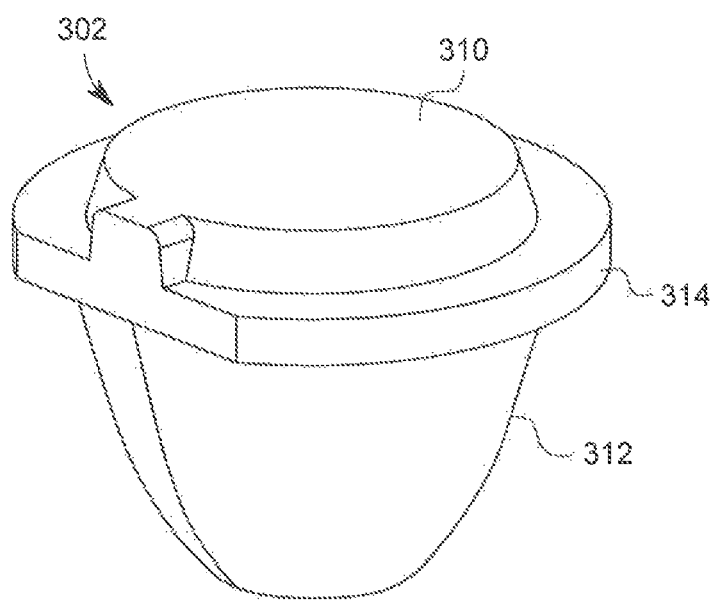
FIG. 7 is a schematic perspective view of a lens employed in the light module depicted in FIG. 6.
Figure 8:
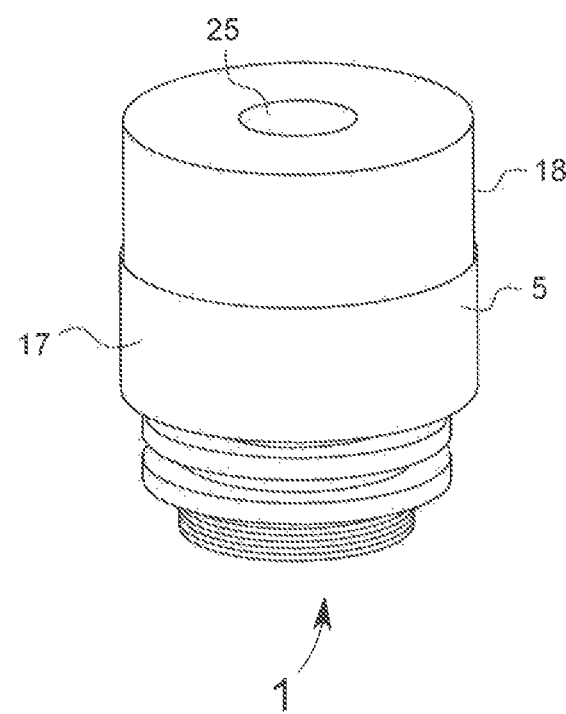
FIG. 8 is a top perspective view of a light module according to another embodiment.
Figure 9:
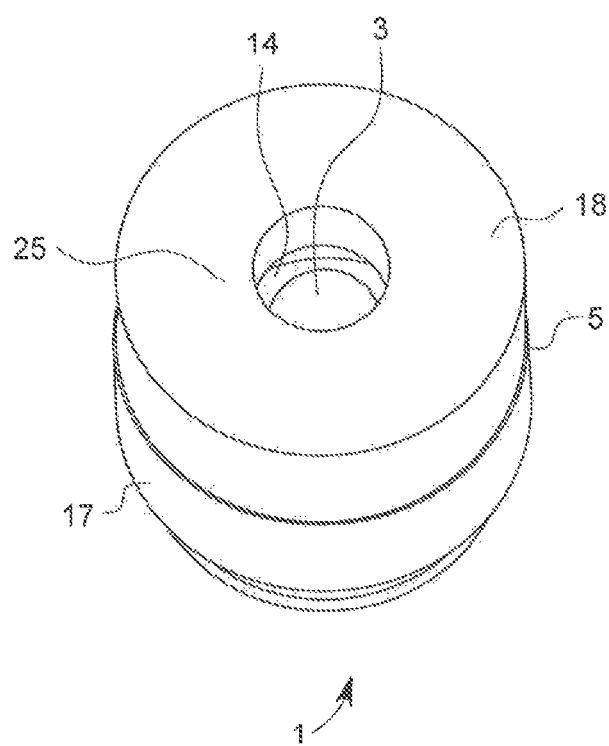
FIG. 9 is another top perspective view of the light module depicted in FIG. 8.
Figure 10:
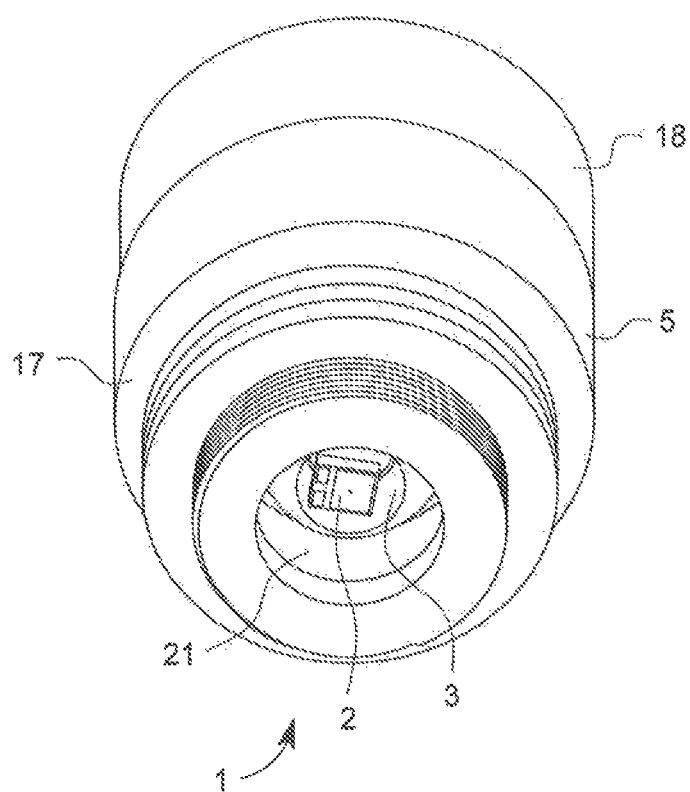
FIG. 10 is a bottom perspective view of the light module depicted in FIG. 8.
Figure 11:
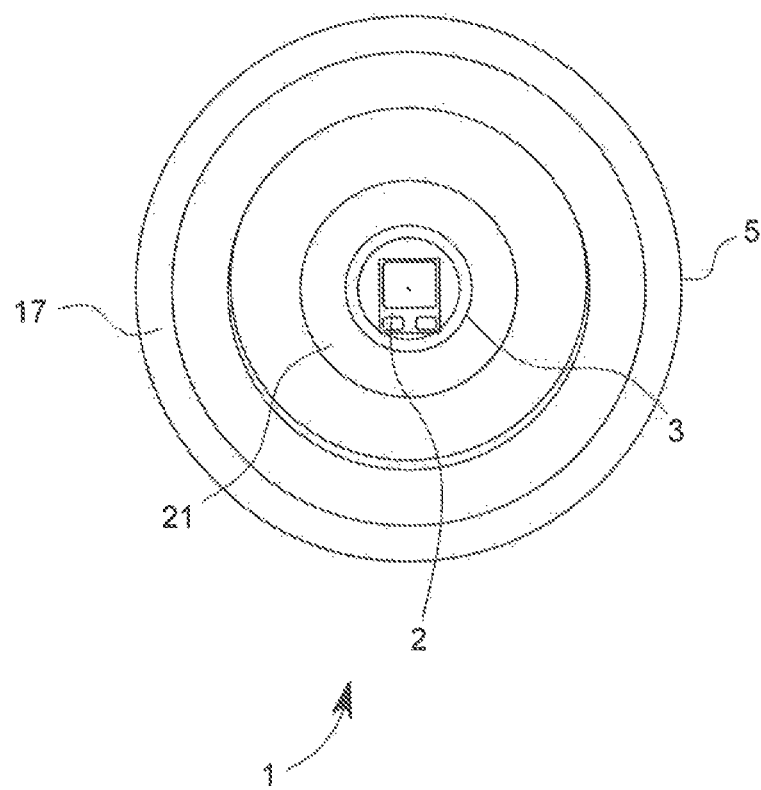
FIG. 11 is a bottom view of the light module depicted in FIG. 8.
Figure 12:
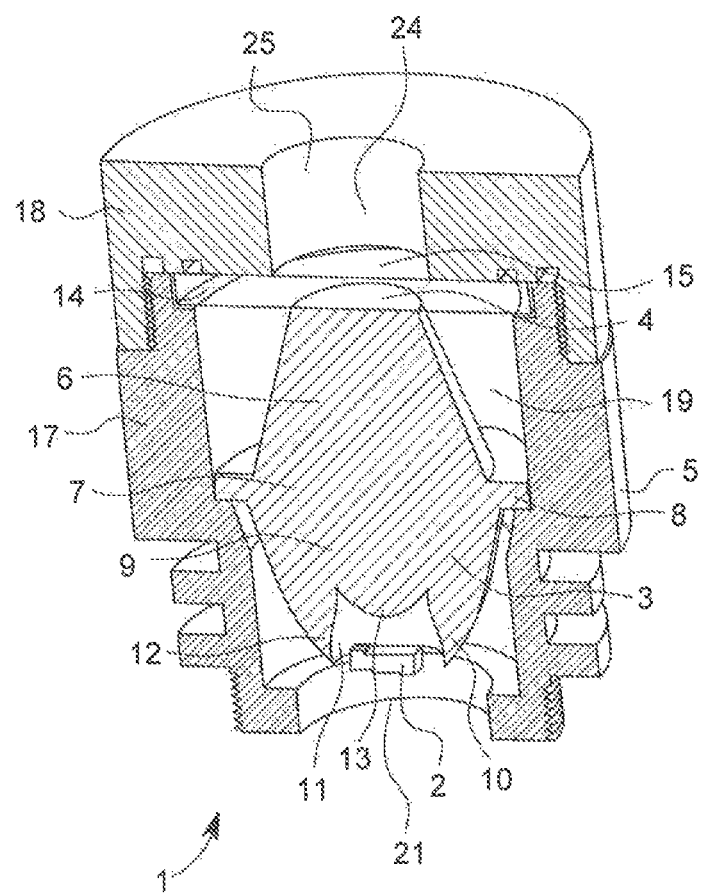
FIG. 12 is a perspective cross-sectional view of the light module.
Figure 13:
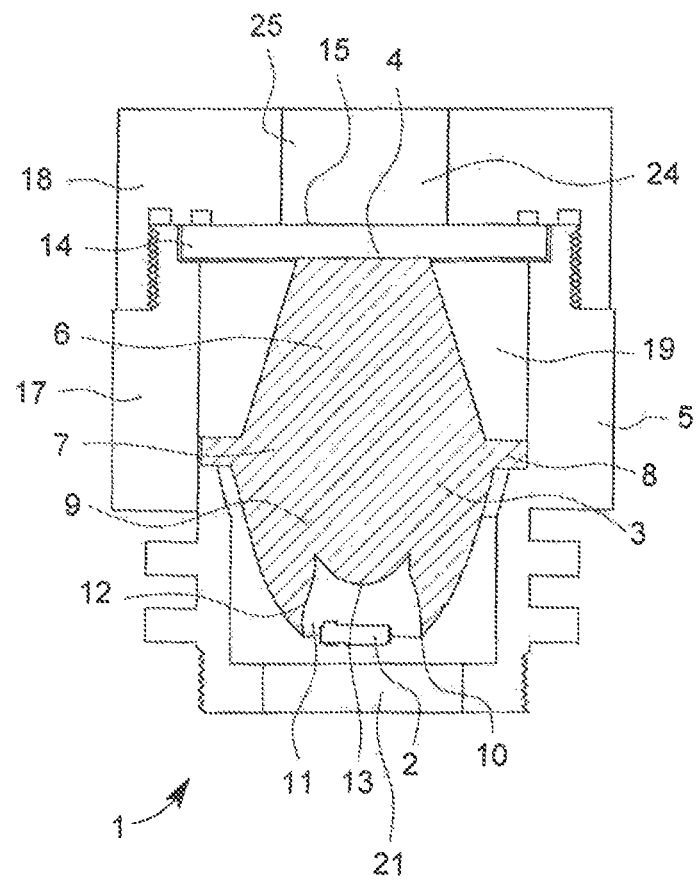
FIG. 13 is a cross-sectional view of the light module.
Figure 14:
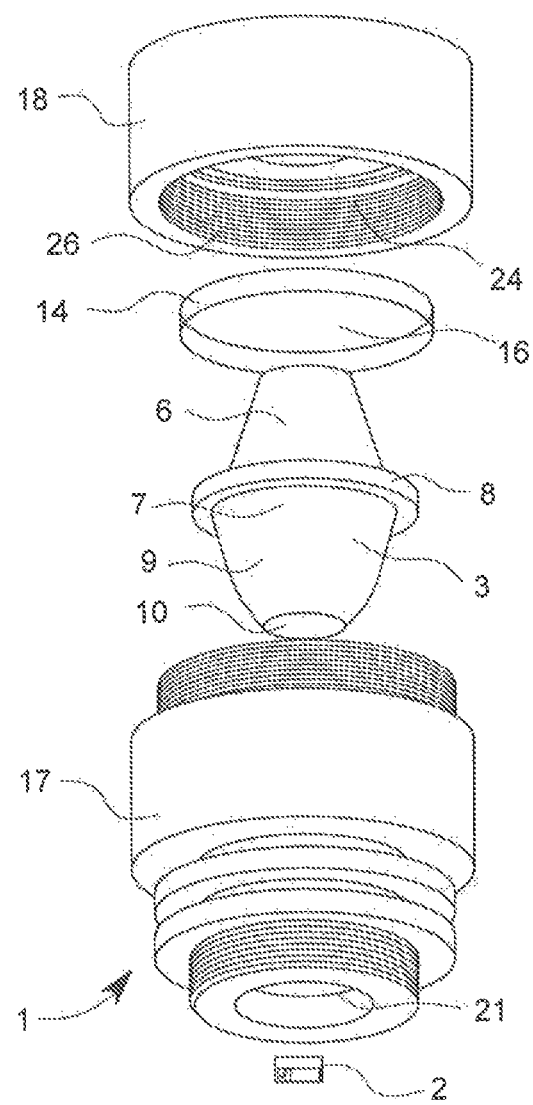
FIG. 14 is a perspective exploded view of the light module.
Figure 15:
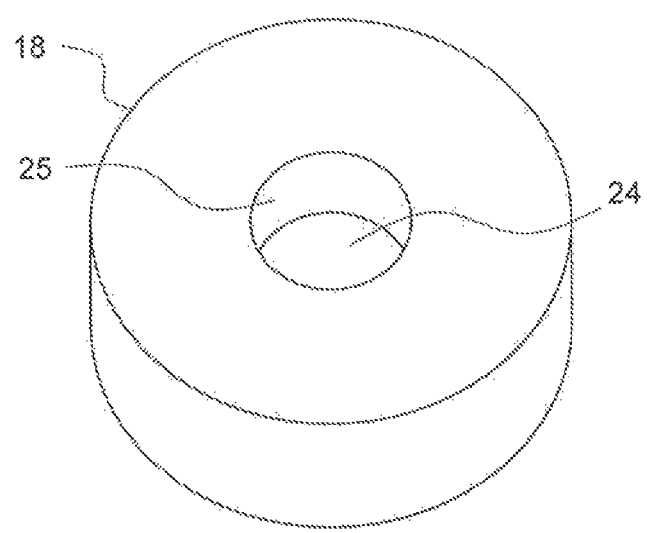
FIG. 15 is a top perspective view of a window ring of the light module.
Figure 16:
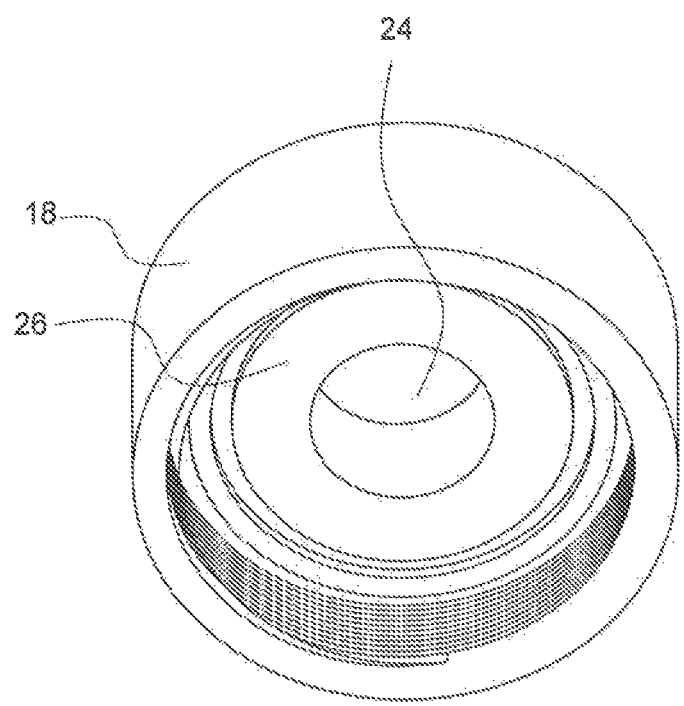
FIG. 16 is a bottom perspective view of the window ring.
Figure 17:
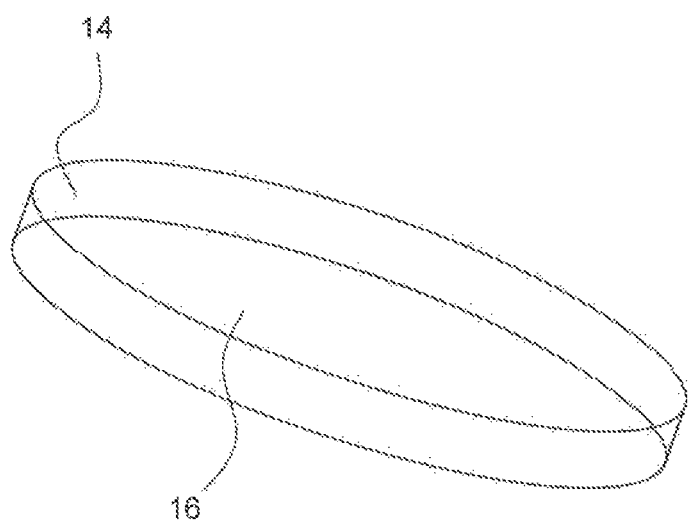
FIG. 17 is a perspective view of an optical window of the light module.
Figure 18:
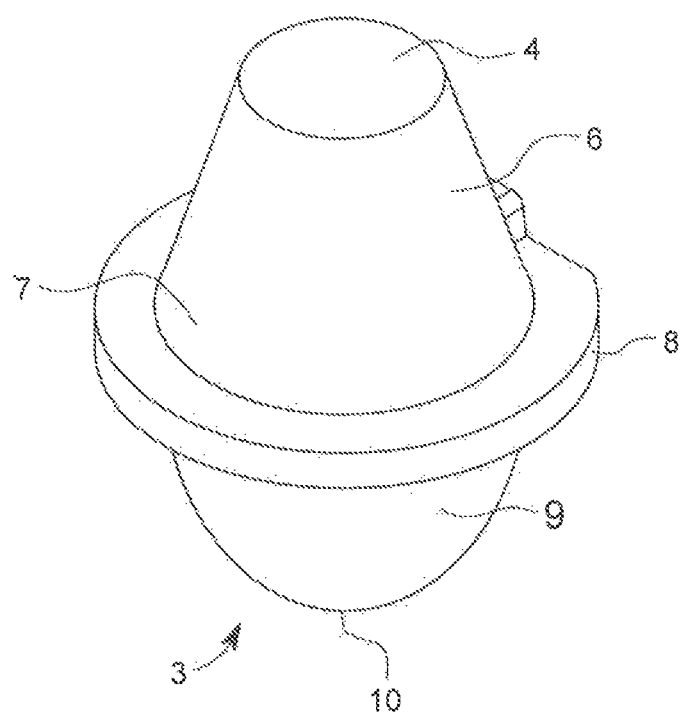
FIG. 18 is a top perspective view of the lens of the light module.
Figure 19:
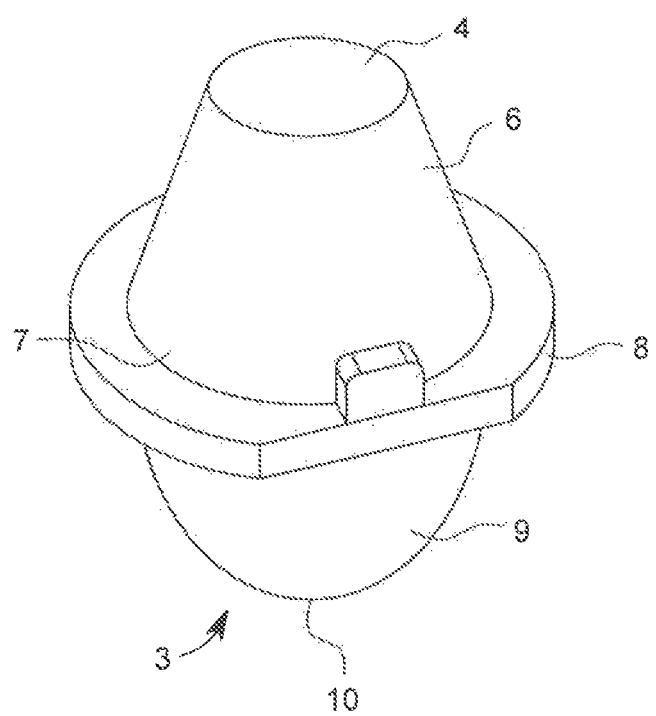
FIG. 19 is another top perspective view of the lens of the light module.
Figure 20:
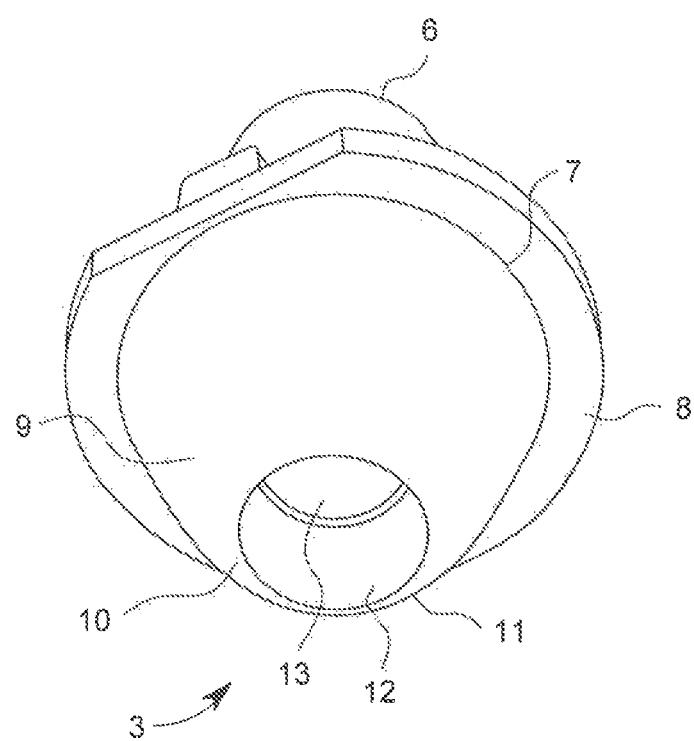
FIG. 20 is a bottom perspective view of the lens of the light module.
Figure 21:
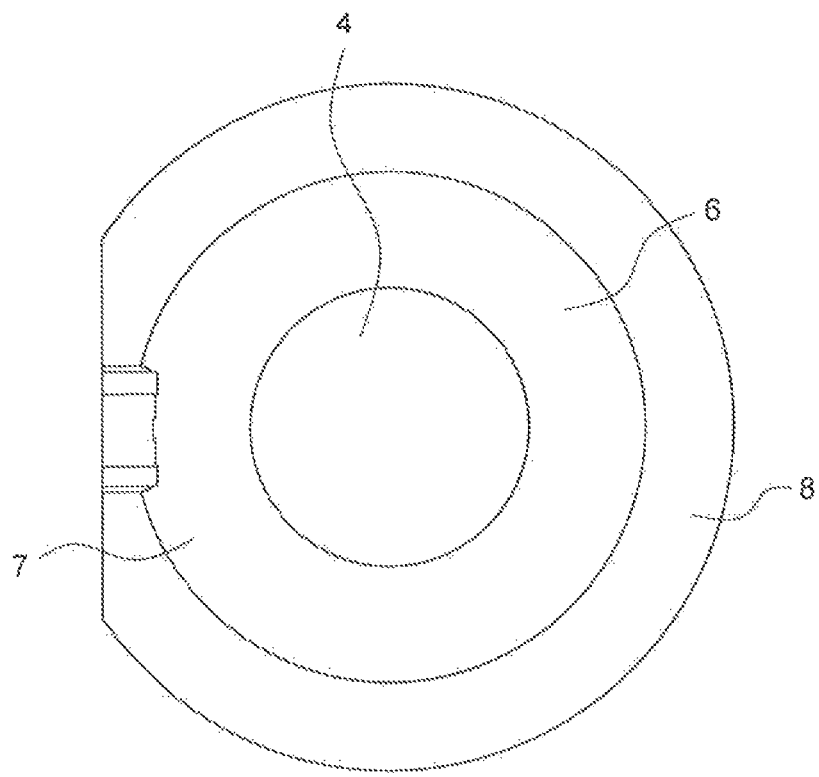
FIG. 21 is a top view of the lens of the light module.
Figure 22:
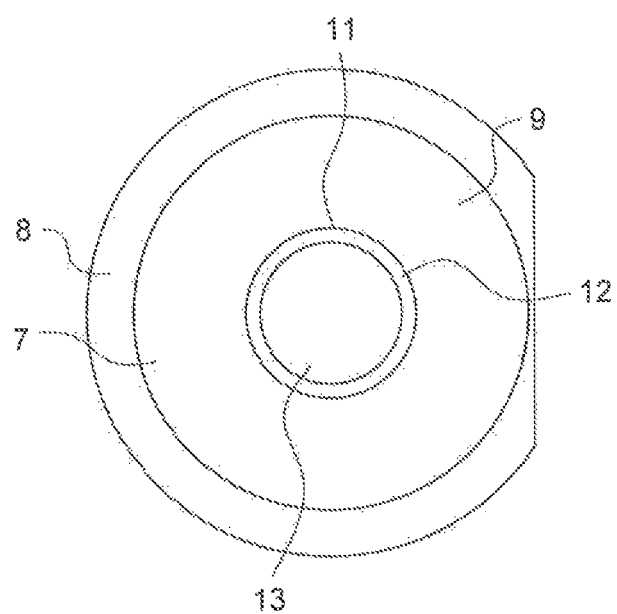
FIG. 22 is a bottom view of the lens of the light module.
Figure 23:
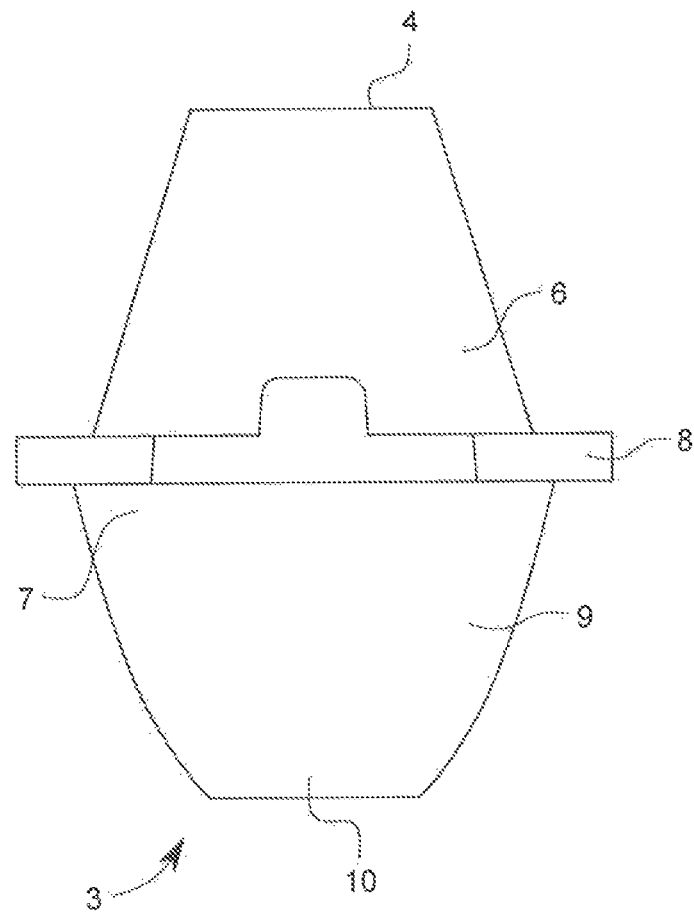
FIG. 23 is side view of the lens of the light module.
Figure 24:
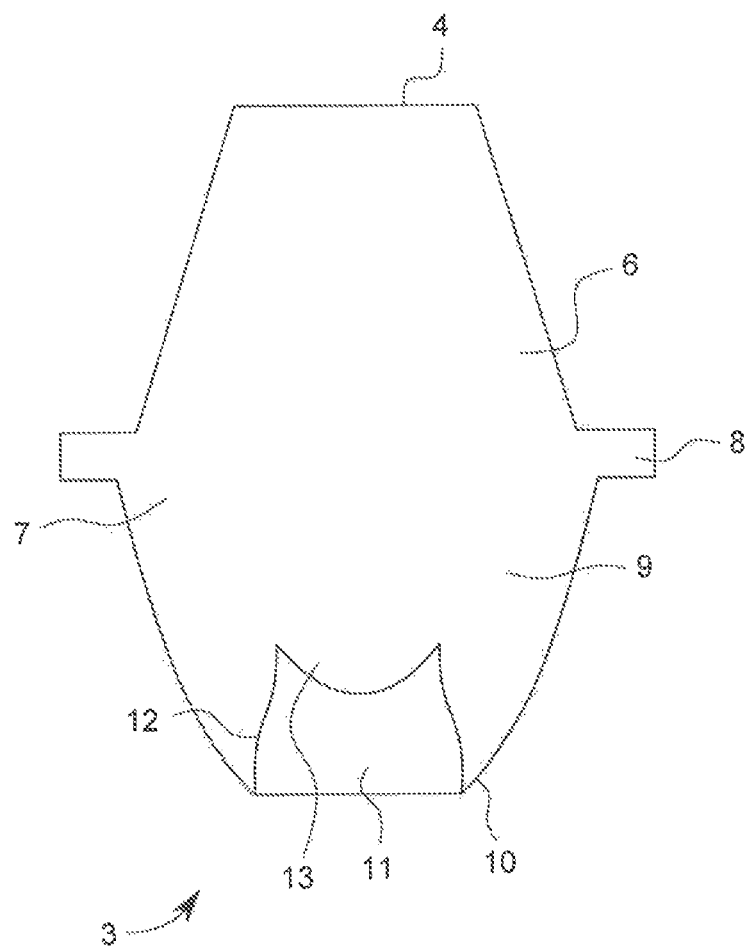
FIG. 24 is a side sectional view of the lens of the light module.
Figure 25:
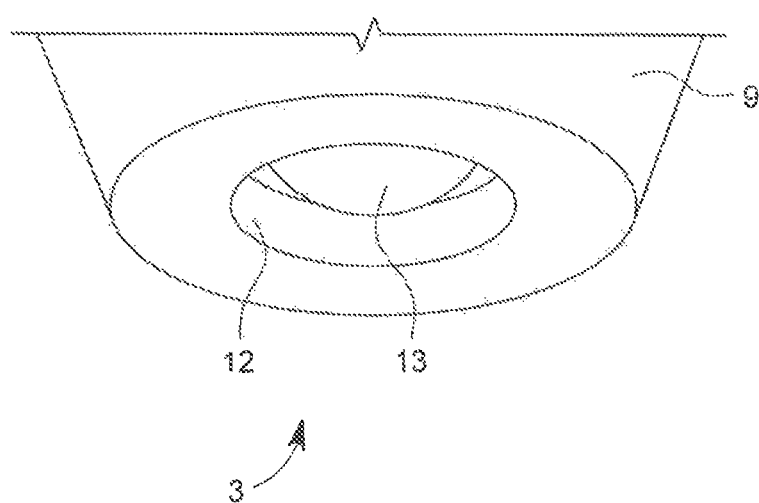
FIG. 25 is a bottom lateral cross-sectional view of the lens of the light module.
Figure 26:
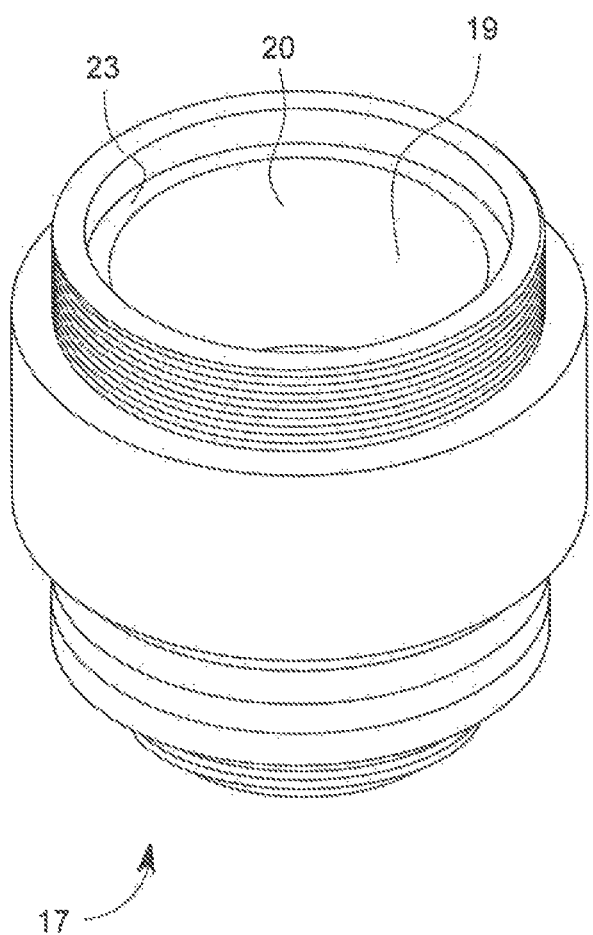
FIG. 26 is a top perspective view of a portion of the housing of the light module configured for holding the lens.
Figure 27:
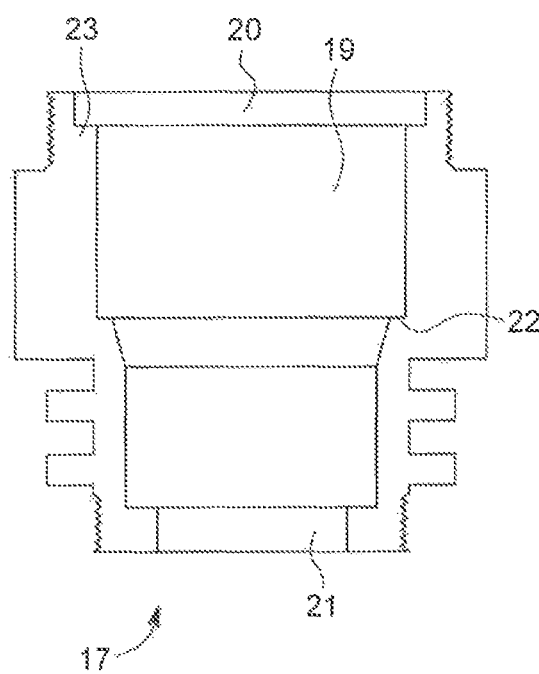
FIG. 27 is a side cross-sectional view of the lens holder depicted in FIG. 26.
Figure 28:
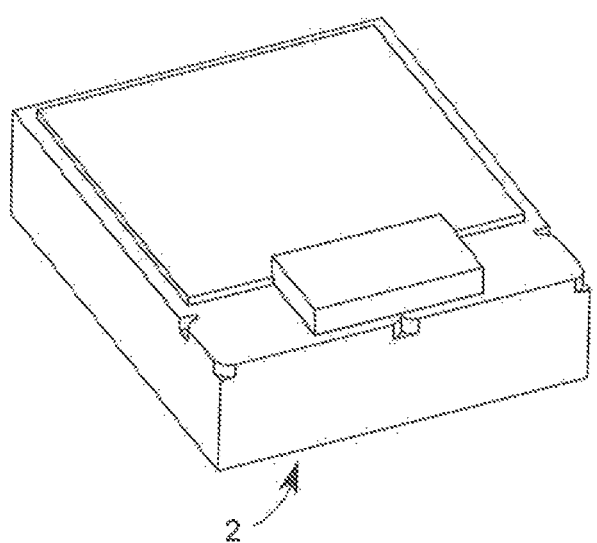
FIG. 28 is a top perspective view of an LED employed in a light module according to an embodiment.
Figure 29:
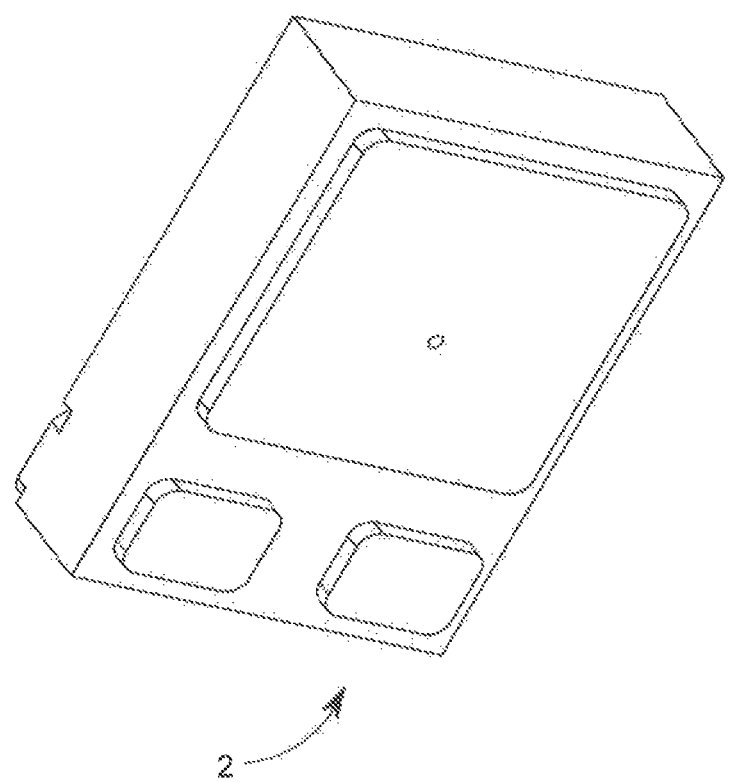
FIG. 29 is a bottom perspective view of the LED depicted in FIG. 28.

With reference to FIGS. 6 and 7, a light module 300 according to another embodiment includes a housing 301 in which a lens 302 can be removably and replaceably positioned. The lens 302 includes an input surface 304 that is optically coupled to an LED 306, which is mounted on a printed circuit board 308, to receive light therefrom. The lens 302 further includes an output surface 310 (which is substantially flat in this embodiment) through which light exits the lens. The lens 302 also includes a peripheral surface 312 that receives at least a portion of the light entering the lens through its input surface and directs the light incident thereon via total internal reflection to the output surface. Similar to the previous embodiment, the peripheral surface 312 is in the form of a truncated ellipse that includes an input focus f1 on or in close proximity of the LED 306 and an output focus f2 that is external to the lens at a distance, e.g., in a range of about 4 mm to about 6 mm, above the lens' output surface 310. In some embodiments, the elliptical peripheral surface 312 can extend from the input surface of the lens to its output surface. In some other embodiments, a proximal portion 312a of the peripheral surface of the lens can have an elliptical shape (e.g., a portion extending from the input surface to a collar 314), and a distal portion 312b of the peripheral surface can have a different shape (e.g., a truncated conical shape).

The collar (herein also referred to as flange) 314 partially encircles the lens body and facilitate the positioning of the lens within the housing 301, as discussed in more detail below.

More specifically, a sleeve 316 in contact with a lower surface of the collar 314 supports the lens 312 above the printed circuit board 308. Another sleeve 318 is seated on an upper surface of the lens collar 314 and supports an optical window 320 at a distance D above the output surface 310 of the lens. The optical window 320 can be implemented, for example, in a manner discussed above in connection with the previous embodiment.

A retaining window 322 is releasably coupled to the housing via a plurality of threads 322a, which engage with respective threads provided in the inner surface of the housing 301. A gasket 322 positioned between the retaining window 322 and the optical window 320 can provide a seal. Similar to the previous embodiment, the retaining window 322 can be connected to an adapter 326 of a light guide (not shown) for optically coupling the light module 300 to the light guide.

The light module 300 includes a pair of electrical leads 300a and 300b for connecting the light module to a source of electrical power, such as one or more batteries.

With reference to FIGS. 8-29, a light module 1 according to the another embodiment includes an external housing 5 having a lens holder 17 and a window ring 8, which are releasably coupled to one another. In this embodiment, the lens holder 17 contains a cylindrical internal channel 19 with a top opening 20 and a bottom opening 21. The lens holder 17 contains an internal shoulder 22 for holding an optical lens 3 within the internal channel 19. The lens holder 17 further includes a second internal shoulder 23 for holding a sapphire window 14 in substantially planar arrangement over an output surface 4 of the optic lens 3. The bottom opening 21 of the lens holder 17 permits any wiring or power sources to be operatively connected to the LEI) 2.

In this embodiment, the optical lens 3 is formed of a single piece of transparent material that allows the passage of the light emitted by the LED 2 therethrough. For example, the lens 3 may be formed of glass, plastic, or sapphire. The lens 3 includes a proximal (or light-receiving) section 9 having an input surface 10 for receiving light from the LED 2, and a distal (or light-outputting) section 6 having a substantially flat output surface 4. The optical lens 3 also includes a collar 8 that can be seated on the internal shoulder 22 for being held within the lens holder 17. The input surface 10 includes a peripheral curved surface 12 and a central convex surface 13 that collectively form a cavity 11. The optical lens 3 includes a peripheral elliptical surface that reflects the light incident thereon via total internal reflection.

The window ring 18 includes a cylindrical internal channel 24 with a top opening 25 and a bottom opening 26. The window ring 18 contacts a top surface 15 of the sapphire window 14 to secure the sapphire window against the internal shoulder 23. In this embodiment, the bottom surface of the window ring 18 and the top surface of the lens holder 17 are threaded for releasable attachment to one another.

The external housing 5 protects the LEI) 2, the elliptical optic lens 3, and the sapphire window 14 from the external environment. The resilient external housing 5 permits the module 1 to be attached to the illumination device without fear of misaligning or damaging the internal LED 2, the elliptical optic lens 3, and the sapphire window 14. In some embodiments, the lens holder 17 and the window ring 18 may be formed of metals, alloys, or plastics.

In some embodiments, the module 1 may be attached to a source of power for supplying electrical power to the LED 2 and any circuitry to provide the correct voltage to the LED 2, both of which are well known in the art. By way of example, the source of power can be one or more batteries, or AC line power.

Similar to the previous embodiments, the light module 1 can be coupled to a light guide, e.g., the light guide of an illumination device, to provide light from the LED 2 to the light guide. Once connected to a power source, the LED 2 emits light that spreads over an angular extent, e.g., an angular extent characterized by a divergence angle of about 160 degrees. The light is received by the lens 3 via the cavity 11. In many embodiments, a large fraction of the light emitted by the LED, and in some cases all the light emitted by the LED, is captured by the input surface 10 of the lens 3. The light entering the lens is transmitted via internal reflection by its peripheral elliptical surface or directly to its output surface 4 and exits through that output surface. In some embodiments, the light exits the lens with a divergence angle less than the divergence angle associated with the light emitted by the LED. For example, the divergence angle associated with the light exiting the lens can be about 30%, 40%, 50%, 60%, or 70% less than the divergence angle of the light emitted by the LED. For example, in some embodiments, the light emitted by the LED 2 can be characterized by a divergence angle of about 160 degrees and the light exiting the lens can be characterized by a divergence angle of about 66 degrees. The light exiting the lens passes through the sapphire window to be coupled to a light guide.

The substantially planar top surface 4 of the elliptical lens 3 is placed in contact with the substantially planar bottom surface 16 of the sapphire window 14, or as close to this surface as mechanically possible. Ideally, both surfaces are as flat as possible, which accomplishes good contact or very minute separation across all or a substantial portion of the interface between the planar surfaces. The emitted light is transferred from the lens 3 to the sapphire window 14.

In some embodiments, the output surface 4 of the lens 3 can be index matched with the substantially planar bottom surface 16 of the sapphire window 14. For example, in some embodiments, refractive index-matching materials, such as a liquid, a gel, or an adhesive cement, can be utilized to provide a refractive index match between the output surface 4 of the lens 3 and the bottom surface 16 of the sapphire window.

Further, in some embodiments, the planar top surface 15 of the sapphire window 14 can be index matched with the input surface of the light guide, e.g., input light guide of an illumination system. In some embodiments, the input light guide of the illumination device can have a flat input face, ideally filling the entire emitting area of planar top surface 15 of the sapphire window 14. The input light guide face is placed in contact with the planar top surface 15 of the sapphire window 14 or as close to this surface as mechanically possible. Ideally, both surfaces are flat to facilitate good contact between them. The flexibility of the input light guide may assist in a higher degree of contact between the two surfaces. This ensures efficient coupling of light out of the planar top surface 15 of the sapphire window 14 into input light guide.

In embodiments of the subject invention, the planar top surface 15 of the sapphire window 14 may have an index-matching material such as a liquid, cement (adhesive), or gel, to substantially match the index of refraction of the input light guide to further improve the light coupled into the light guide.

In some embodiments, the light guide can be a single light guide fiber, a plurality of square or round light guide fibers, liquid light guides, a plurality of plastic or glass fibers coupled to form a light guide, a plurality of plastic or glass rods coupled to form a light guide, a plurality of tapers made from glass or plastic fibers coupled to form a light guide, or a plurality of solid tapers made from glass or plastic coupled to form a light guide.

The emitted light is transferred from the sapphire window 14 to the light guide. As a result, a greater amount of light from the LED 2 can be transmitted to the distal end of the light guide to illuminate objects under investigation, e.g., in an endoscope system.

The lack of additional optics between the LED 2, the elliptical optic lens 3, and the sapphire window 14 simplifies the mechanical design and space requirements for the module 1 allowing, for example, easier insertion into existing illumination devices. In some embodiments, small batteries may be used to power the LED 2, thus permitting the light module to be used in compact illumination device while providing a desired illumination.

Those having ordinary skill in the art will appreciate that various changes can be made to the above embodiments without departing from the scope of the invention. Further, various elements of one embodiment can be incorporate in another embodiment. For example, the lens of one embodiment may be incorporate into another embodiment.

What is claimed is:

1. A light module, comprising:
   a housing providing a hollow chamber extending from a proximal end to a distal end,
   a lens positioned in the hollow chamber, the lens having a lens body comprising an input surface for receiving light from a light source and an output surface through which light exits the lens,
   a pair of sleeves disposed on opposite sides of the lens,
   an adapter configured for removable and replaceable coupling to the distal end of the hollow chamber of the housing, the adapter being further configured for receiving a proximal part of a light guide such that the light guide is secured within the adapter so as to receive at least a portion of the light exiting the output surface of the lens.

2. The light module of claim 1, further wherein said adapter comprises an opening on a lateral surface thereof for receiving a retaining pin for securing the light guide within the adapter.

3. The light module of claim 1, wherein said adapter comprises a housing having a plurality of external threads for engaging with a plurality of internal threads disposed at an end of said hollow chamber for coupling the adapter to the hollow chamber.

4. The light module of claim 1, wherein said hollow chamber is substantially cylindrical.

5. The light module of claim 1, wherein said light guide comprises an optical fiber.

6. The light module of claim 1, wherein said light guide comprises a bundle of optical fibers.

7. The light module of claim 1, wherein said light module comprises a retaining window.

8. The light module of claim 7, wherein said retaining window comprises a plurality of internal threads for engaging with said external threads of said hollow chamber for coupling the adapter to said hollow chamber.

* * * * *